United States Patent [19]

Wenzel et al.

[11] 4,155,922
[45] May 22, 1979

[54] PROCESS FOR THE PURIFICATION OF CRUDE ANTHRAQUINONE

[75] Inventors: Rupert Wenzel; Johann Grolig, both of Leverkusen, Fed. Rep. of Germany

[73] Assignee: Bayer Aktiengesellschaft, Leverkusen, Fed. Rep. of Germany

[21] Appl. No.: 850,511

[22] Filed: Nov. 10, 1977

[30] Foreign Application Priority Data

Dec. 4, 1976 [DE] Fed. Rep. of Germany ....... 2655082

[51] Int. Cl.$^2$ .............................................. C07C 49/68
[52] U.S. Cl. .................................... 260/369; 260/707
[58] Field of Search ................................. 260/369, 707

[56] References Cited

U.S. PATENT DOCUMENTS

| | | | |
|---|---|---|---|
| 1,591,712 | 7/1926 | Lewis ................................... | 260/369 |
| 3,505,361 | 4/1970 | Greco ................................... | 260/369 |
| 3,870,730 | 3/1975 | Scharfe et al. ....................... | 260/369 |
| 4,036,860 | 7/1977 | Engelbach et al. .................. | 260/369 |

FOREIGN PATENT DOCUMENTS 1217283 3/1960 France ..................................... 260/369

*Primary Examiner*—Allen B. Curtis
*Assistant Examiner*—Raymond Covington
*Attorney, Agent, or Firm*—Sprung, Felfe, Horn, Lynch & Kramer

[57] ABSTRACT

A process has been provided for the purification of crude anthraquinone made by (1) oxidation of naphthalene to naphthoquinone (2) reaction of the oxidation product with butadiene to give tetrahydroanthraquinone and (3) oxide-hydrogenation of this reaction product with molecular oxygen to yield the crude anthraquinone, then optionally separating naphthalene, phthalic anhydride and low-boiling compounds from said crude anthraquinone. The purification of said crude anthraquinone is effected by treatment with an oxygen compound or mixture of oxygen compounds of the elements of the 1st and/or 2nd main group of the periodic system at elevated temperature, if desired in the presence of an inert solvent and the purified anthraquinone is isolated by physical separation methods from the products treated.

18 Claims, No Drawings

PROCESS FOR THE PURIFICATION OF CRUDE ANTHRAQUINONE

The present invention relates to a process for the purification of crude anthraquinone by treating the crude anthraquinone with inorganic oxygen compounds of the elements of the first and/or second main groups of the periodic system.

It is known to purify anthraquinone, which has been prepared, for example, by chromic acid oxidation or atmospheric oxidation of anthracene, by crystallisation, for example from nitrobenzene, or by sublimation (Ullmann's Enzyklopadie der technischen Chemie (Ullmann's Encyclopaedia of industrial Chemistry), 4th edition, volume 7, page 581 and 583).

However, these methods cannot be used, for example, in the case of crude anthraquinone obtained, as the sump product, according to British Patent Specification No. 1,394,009 since the highly coloured and high-boiling impurities possess a similar solubility to anthraquinone and thus cannot be removed by simple crystallisation. On the other hand, some of the compounds present as impurities are volatile, so that purification of the anthraquinone, for example by distillation or sublimation, industrially is very expensive and associated with high losses of anthraquinone.

A process has now been found for the purification of crude anthraquinone, which has been obtained by oxidation of naphthalene to naphthoquinone, reaction of the oxidation product with butadiene to give tetrahydroanthraquinone, oxidehydrogenation of this reaction product with molecular oxygen to give a crude anthraquinone and, if appropriate, separating off of naphthalene, phthalic anhydride and low-boiling compounds from this crude anthraquinone, in which the crude anthraquinone is treated with an oxygen compound or mixture of oxygen compounds of the elements of the first and/or second main group of the periodic system (as printed in Emelius, Anderson, Modern Aspects of Inorganic Chemistry, London 1954, page 2) at elevated temperature, optionally in the presence of an inert solvent, and purified anthraquinone is isolated by physical separation methods from the products thus treated.

The abovementioned oxygen compounds are employed, depending on the content of impurities in the crude anthraquinone in effective amounts up to about 20% by weight or more specially, in amounts of about 0,1 to 20% by weight, in particular 1 to 10% by weight, relative to the crude anthraquinone to be purified.

Suitable oxygen compounds of the elements of the first and second main group of the periodic system are, for example, the oxides, hydroxides, carbonates, bicarbonates and carboxylates of the alkali and alkaline earth metals, such as lithium, sodium, potassium, magnesium, calcium, strontium and barium.

The oxides and/or hydroxides of the elements of the first and second main group of the periodic system are particularly suitable, sodium hydroxide, calcium hydroxide and/or calcium oxide being preferably employed.

Mixtures of oxides and/or hydroxides of the elements of the first and second main group of the periodic system are particularly effective, for example mixtures of alkali and alkaline earth metal oxides and/or hydroxides, such as mixtures of sodium hydroxide and calcium oxide or sodium hydroxide and calcium hydroxide.

In general, the ratio in the mixture of oxides to hydroxides is approximately in the range from 1:10 to 10:1. However, the ratio in the mixture is variable, so that, for example, in the sodium hydroxide/calcium oxide mixture the cheaper calcium oxide can substantially replace the more expensive sodium hydroxide.

In general, the treatment of the crude anthraquinone is carried out in a temperature range from about 150 to about 400° C., the temperature range from about 200 to about 350° C. being preferred.

Depending on the reaction temperature used and the mixing conditions, the reaction times are between a few minutes and several hours. In general, reaction times of about 5 minutes to about 1 hour are sufficient.

The heat treatment of the crude anthraquinone with the oxygen compounds mentioned can be carried out without a solvent (method A) or in the presence of an organic solvent (method B) which is inert towards the compounds added and should dissolve as little as possible of the residues present as impurities. As used throughout the text and claims the term "inert solvent" has this meaning.

A preferred way of carrying out the reaction is the heat treatment of crude anthraquinone, in the absence of a solvent, with, for example, preferably about 1 to 10% by weight of sodium hydroxide or a mixture of sodium hydroxide and calcium oxide or calcium hydroxide, at temperatures of about 250 to about 350° C. (method A). The treatment can be carried out discontinuously or continuously in an appropriate mixing device, for example in a mixing screw. The reaction time is shortened to about 5 to 10 minutes by intimately mixing the product.

The heat treatment of crude anthraquinone can also be carried out in the presence of inert solvents (method B). Inert, organic solvents which have, at elevated temperatures, a certain dissolving power for the oxygen-containing additives, for example oxidic additives, and/or anthraquinone, but on the other hand dissolve as little as possible of the undistillable compounds present in the crude anthraquinone and formed during the heat treatment are particularly suitable. In general, low temperatures in the range from about 150 to about 400° C., for example temperatures of about 150 to about 250° C., are sufficient in the presence of these solvents.

Suitable inert solvents are, for example, high-boiling monohydric or polyhydric, particularly dihydric, aliphatic or cycloaliphatic alcohols and/or phenol, which can be substituted by alkyl groups with up to 6 C-atoms.

Hexanol, ethylene glycol, propylene glycol, butane-1,4-diol and butane-1,2-diol may be mentioned as examples of aliphatic alcohols; cyclohexanol as an example of cycloaliphatic alcohols and phenol and cresol as examples of phenols.

Phenol or cresol are preferably employed as the inert solvent.

The heat treatment of the crude anthraquinone can be carried out with the inert solvents mentioned under reflux temperature under normal pressure or increased or reduced pressure, the process preferably being carried out under normal pressure. The obtaining of anthraquinone in the pure form can be carried out in a simple manner by crystallisation from the inert solvent used, if appropriate with the addition of a further solvent.

If the heat treatment of the crude anthraquinone is carried out without a solvent (method A), the subsequent isolation of the purified anthraquinone can be carried out in various manners by physical separation methods which are generally customary. For example, anthraquinone can be separated off from the high-boiling residues by thin film distillation and obtained in high purity. A further preferred embodiment of the anthraquinone separation is sublimation. It can be carried out under reduced pressure or in the presence of a carrier gas under normal pressure or slightly increased pressure. Suitable carrier gases are, for example, nitrogen and/or carbon dioxide.

The residues formed in the purification of crude anthraquinone are obtained in a form which can be easily split off and conveyed. Evaporation in suitable apparatuses, for example in an evaporating screw, is also possible.

A further possibility for isolating the anthraquinone from the treated product is extraction with an inert solvent in which anthraquinone is readily soluble at elevated temperature and, is necessary, elevated pressure, but which does not dissolve the high-molecular products and the additives. Anthraquinone is crystallised out from the solvent by cooling, filtered off and, after washing and drying, isolated in the pure form. A certain proportion of the inert solvent is freed from dissolved impurities by redistillation.

Suitable inert solvents for the extraction are, in addition to the alcohols and phenols already mentioned, above all those inert solvents which dissolve anthraquinone well at higher temperatures and poorly at low temperatures, are inert towards the additives and do not dissolve the high-molecular impurities and excess additives which are to be separated off.

Saturated aliphatic and cycloaliphatic hydrocarbons as well as aromatic and araliphatic hydrocarbons with 6 to 20 C atoms, which can be optionally monosubstituted or polysubstituted by alkyl groups with 1 to 12 C atoms, are particularly suitable.

Examples of saturated aliphatic hydrocarbons to be mentioned are: hexane, heptane, octane, isooctane and isododecane; of cycloaliphatic hydrocarbons: cyclohexane, methylcyclohexane, dimethylcyclohexane and decalin; of aromatic hydrocarbons: benzene, toluene, xylene, ethylbenzene, cumene and trimethylbenzenes and of araliphatic hydrocarbons: tetralin, indane and methylindane.

Alkyl groups by which the abovementioned hydrocarbons can be substituted are, for example, methyl, ethyl, propyl, butyl, isopropyl, sec.-butyl, tert.-butyl, pentyl, hexyl, octyl, isooctyl and isododecyl groups.

The following hydrocarbons can be advantageously be employed, for example, as the inert solvent for the extraction: benzene, toluene, xylene, tetralin, decalin, isooctane, isododecane, cyclohexane and methylcyclohexane.

Hydrocarbons can be employed as the inert solvent both by themselves and in combination with one another.

A particularly preferred inert solvent is xylene, in parcular in the form of the industrial isomer mixture, which can be employed for the extraction, for example, in a 8-fold to 20-fold excess, expressed in parts by weight of xylene to parts by weight of crude anthraquinone. Further details for carrying out the extraction and the crystallisation are the state of the art and do not need to be specially given.

The various abovementioned variants of the anthraquinone purification according to the invention are illustrated in the following Examples.

EXAMPLE 1

A crude anthraquinone of the following composition was used (% by weight):
phthalic anhydride: 1
sum of the unknown compounds: 3.5
anthraquinone: 75.5
residues: 20

50 g of this crude anthraquinone were finely ground and 2.5 g (5% by weight, relative to the crude anthraquinone) of pulverised sodium hydroxide were added. The mixture was heated to 300° C. in a three-necked stirred flask, whilst stirring vigorously, whereupon some of the product melted, and was kept at this temperature for 1 hour. After cooling to room temperature, the mass was finely ground.

10 g of this product were sublimed under 1 mm Hg and at 250° C. in the course of 2 hours. The anthraquinone contained in the crude anthraquinone was almost quantitatively obtained as a yellow sublimate of melting point 286° C. Analysis of the sublimate by gas chromatography gave an anthraquinone content of 100%. No further impurities could be detected either by gas chromatography or by liquid chromatography.

A further 10 g of the finely ground crude anthraquinone pretreated as above were extracted with 200 g of xylene (industrial isomer mixture) under reflux (140° C.) for 20 minutes. The residue was rapidly filtered off on a heated filter and the filtrate was crystallised at 0° C. The mixture was filtered and the anthraquinone crystals were rinsed with twice 10 ml of xylene and dried under 200 mm Hg and at 150° C. 6.9 g of light yellow anthraquinone of melting point 286° C. were obtained (96% of theory, relative to the crude anthraquinone). No impurities of any kind could be detected either by gas chromatography or by liquid chromatography. The product could be sublimed completely.

EXAMPLE 2 (Comparison Example)

Crude anthraquinone of the composition indicated in Example 1 was directly extracted hot (at the reflux temperature ) with the following solvents without additives and without a heat-pretreatment, and was crystallised:xylene (industrial isomer mixture), nitrobenzene, chlorobenzene and sulpholane.

A further sample of crude anthraquinone which had not been pretreated was sublimed under 1 mm Hg and at 250° C. for 2 hours. From all these samples, in each case 5 g of crude anthraquinone were employed and for the extraction 100 g of solvent were employed. The following table shows the results of the extraction:

| Solvent | Extraction yield of anthraquinone (% of theory) | Colour of the crystallised anthraquinone |
|---|---|---|
| xylene (industrial) | 98 | red |
| nitrobenzene | 98 | red |
| chlorobenzene | 99 | red |
| sulpholane | 98 | red |

From this table it can be seen that in the extraction without the pretreatment according to the invention, the highly coloured constituents pass over into the anthraquinone, so that the anthraquinone is unusable for further use in the dyestuff field.

In the sublimation, a highly impure anthraquinone was also obtained which, in addition to traces of phthalic anhydride, still contained 1.1% of unknown compounds. It was likewise unusable for further processing to dyestuffs.

EXAMPLE 3

A crude anthraquinone of the composition indicated in Example 1 was treated with 20% by weight of calcium oxide at 300° C. as described in Example 1. At intervals of 1 hour a sample was removed and sublimed and the sublimate was analysed. The following result was obtained:

| Time (hours) | Content of unknown compounds (%) | Colour |
| --- | --- | --- |
| 1 | 1.1 | red |
| 2 | 0.3 | red |
| 3 | 0.0 | light yellow |

EXAMPLE 4

10% by weight of calcium hydroxide, relative to the crude anthraquinone, were added instead of calcium oxide and the mixture was treated for 2 hours, whilst stirring, as described in Example 1.

After extraction and crystallistion from xylene, pure anthraquinone was obtained in a yield of 95% of theory.

EXAMPLES 5 to 10

The heat treatment was carried out with mixtures of sodium hydroxide and calcium hydroxide under various conditions. The anthraquinone samples which had been subjected to a heat treatment were extracted with xylene in the ratio of 1 part by weight of crude anthraquinone to 20 parts by weight of xylene and crystallised. The following results were obtained:

| No. | Addition (% by weight relative to the crude anthraquinone) | | Temperature °C | Time hours | Crystalline anthraquinone Yield % of theory (relative to crude anthraquinone) | Unknown compounds | |
| --- | --- | --- | --- | --- | --- | --- | --- |
|  | NaOH | CaO |  |  |  | % | Colour |
| 5 | 0.5 | 5 | 300 | 2 | 95 | 0.01 | dark yellow |
| 6 | 1 | 5 | 300 | 2 | 91 | 0.0 | light yellow |
| 7 | 1 | 5 | 280 | 2 | 90 | trace | yellow |
| 8 | 2 | 5 | 320 | 2 | 99 | 0.0 | light yellow |
| 9 | 1 | 5 | 320 | ½ | 99 | 0.0 | light yellow |
| 10 | 1 | 5 | 350 | ½ | 70 | 0.0 | light yellow |

EXAMPLE 11

10 g of crude anthraquinone having the composition indicated in Example 1 were digested in 20 g of freshly distilled m-cresol and 0.5 g of calcium oxide and 0.1 g of sodium hydroxide were added. The mixture was heated to the reflux temperature and kept at the reflux for 4 hours, whilst stirring vigorously. After adding 100 ml of xylene, the mixture was again briefly heated to the boil and the residue was filtered off. Yellow anthraquinone (85% of theory), in which no further impurities could be detected, was obtained from the filtrate.

What is claimed is:

1. Process for the purification of crude anthraquinone, obtained by oxidation of naphthalene to naphthaquinone, reaction of the oxidation products with butadiene to give tetrahydroanthraquinone, oxidehydrogenation of this tetrahydroanthraquinone reaction product with molecular oxygen to give a crude anthraquinone and, if desired, separating off of naphthalene, phthalic anhydride and low-boiling compounds from this crude anthraquinone, which comprises treating said crude anthraquinone with an oxygen compound or a mixture of oxygen compounds of an element of the 1st or 2nd main group of the periodic system said compound or compounds being oxides, hydroxides, carbonates, bicarbonates or carboxylates of the alkali and alkaline earth metals at temperatures of about 150 to about 400° C., in the presence or absence of an inert solvent, and isolating purified anthraquinone by physical separation methods from the reaction mixture.

2. Process according to claim 1 wherein said oxygen compounds are alkali metal or alkaline earth metal oxides or hydroxides.

3. Process according to claim 1 wherein treatment of said crude anthraquinone with an oxygen compound or mixture of oxygen compounds of an element of the 1st or 2nd main group of the periodic system at elevated temperature is carried out in the absence of an inert solvent at a temperature of about 250° to about 350° C.

4. Process according to claim 3 wherein said oxygen compounds are alkali metal or alkaline earth metal oxides or hydroxides.

5. Process according to claim 4 wherein said oxygen compounds are alkali metal oxides, alkali metal hydroxides or a mixture of alkali metal oxides and hydroxides.

6. Process according to claim 4 wherein said oxygen compounds are calcium oxide, calcium hydroxide or mixtures of calcium oxide and calcium hydroxide.

7. Process according to claim 4 wherein said oxygen compounds are mixtures of alkali metal oxides and/or alkali metal hydroxides with calcium oxide and/or calcium hydroxide.

8. Process according to claim 7 wherein sodium oxide is the alkali metal oxide and sodium hydroxide is the alkali metal hydroxide.

9. Process according to claim 1 wherein treatment of said crude anthraquinone with an oxygen compound or mixture of oxygen compounds of an element of the 1st or 2nd main group of the periodic system is carried out in the presence of an inert solvent at a temperature of about 150 to about 250° C.

10. Process according to claim 9 wherein said oxygen compounds are alkali metal or alkaline earth metal oxides or hydroxides.

11. Process according to claim 10 wherein said oxygen compounds are alkali metal oxides, alkali metal hydroxides or a mixture of alkali metal oxides and hydroxides.

12. Process according to claim 10 wherein said oxygen compounds are calcium oxide, calcium hydroxide or mixtures of calcium oxide and calcium hydroxide.

13. Process according to claim 10 wherein said oxygen compounds are mixtures of alkali metal oxides and/or alkali metal hydroxides with calcium oxide and/or calcium hydroxide.

14. Process according to claim 13 wherein sodium oxide is the alkali metal oxide and sodium hydroxide is the alkali metal hydroxide.

15. Process according to claim 9 wherein the inert solvent is phenol or cresol.

16. Process according to claim 1 wherein the purified anthraquinone is isolated by distillation.

17. Process according to claim 1 wherein the purified anthraquinone is isolated by sublimation.

18. Process according to claim 1 wherein the purified anthraquinone is isolated by extraction with an inert solvent at elevated temperature and subsequent crystallization.

* * * * *